(12) United States Patent
Krekeler et al.

(10) Patent No.: US 11,123,300 B2
(45) Date of Patent: Sep. 21, 2021

(54) IMMEDIATE RELEASE TABLET OF A BENZOTHIOPHENE COMPOUND

(71) Applicant: Hexal AG, Holzkirchen (DE)

(72) Inventors: Andreas Krekeler, Holzkirchen (DE); Dimitri Neumann, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 138 days.

(21) Appl. No.: 16/325,276

(22) PCT Filed: Aug. 11, 2017

(86) PCT No.: PCT/EP2017/070422
§ 371 (c)(1),
(2) Date: Feb. 13, 2019

(87) PCT Pub. No.: WO2018/033481
PCT Pub. Date: Feb. 22, 2018

(65) Prior Publication Data
US 2020/0069593 A1 Mar. 5, 2020

(30) Foreign Application Priority Data
Aug. 16, 2016 (EP) .................................. 16184404

(51) Int. Cl.
*A61K 9/20* (2006.01)
*A61K 9/28* (2006.01)
*A61K 31/496* (2006.01)

(52) U.S. Cl.
CPC .......... *A61K 9/2077* (2013.01); *A61K 9/2054* (2013.01); *A61K 9/2095* (2013.01); *A61K 9/282* (2013.01); *A61K 31/496* (2013.01)

(58) Field of Classification Search
None
See application file for complete search history.

(56) References Cited

U.S. PATENT DOCUMENTS

2014/0234417 A1 * 8/2014 Inoue .................. A61K 31/496
424/474

FOREIGN PATENT DOCUMENTS

| CN | 105106142 A | * | 12/2015 | |
| EP | 2767285 A1 | * | 8/2014 | ............. A61P 43/00 |
| EP | 2767285 A1 | | 8/2014 | |
| IN | 201400035 I4 | * | 7/2015 | |
| WO | 2006112464 A1 | | 10/2006 | |
| WO | 2012137971 A1 | | 10/2012 | |
| WO | 2013054872 A1 | | 4/2013 | |
| WO | 2013162046 A1 | | 10/2013 | |

OTHER PUBLICATIONS

International Search Report and Written Opinion for PCT/EP2017/070422, dated Feb. 22, 2018, 8 pages.

* cited by examiner

*Primary Examiner* — Susan T Tran
(74) *Attorney, Agent, or Firm* — Luedeka Neely Group, P.C.

(57) ABSTRACT

The present invention discloses an immediate release tablet comprising at least a tablet core, wherein the tablet core comprises at most 20% brexpiprazole relative to the total of the tablet core, and at least one pharmaceutically acceptable excipient, wherein the tablet core is made by direct compression. Also disclosed are a batch of such immediate release tablets, and a process for preparing such immediate release tablets.

17 Claims, 2 Drawing Sheets

PVC packaging material transparent (250 μm thick)

Fig. 3

PVC blocking UV specific wavelength (250 μm thick)

IMMEDIATE RELEASE TABLET OF A BENZOTHIOPHENE COMPOUND

This application is a Section 371 national phase entry of PCT application PCT/EP2017/070422, filed Aug. 11, 2017. This application also claims the benefit of the earlier filing date of European patent application 16184404.8, filed Aug. 16, 2016.

FIELD OF THE INVENTION

The present invention relates to an immediate release tablet comprising at least a tablet core, wherein the tablet core comprises a limited amount of brexpiprazole. The present invention also relates to a batch of such immediate release tablets, and to a process for the preparation of an immediate release tablet comprising brexpiprazole.

BACKGROUND OF THE INVENTION

7-[4-[4-(1-Benzothiophen-4-yl)piperazin-1-yl]butoxy]quinolin-2(1H)-one (brexpiprazole; compound I) is an antidepressant and antipsychotic drug marketed under the brand Rexulti® for the oral treatment of schizophrenia and as an adjunctive treatment to antidepressants in major depressive disorder. REXULTI tablets are intended for oral administration and available in 0.25 mg, 0.5 mg, 1 mg, 2 mg, 3 mg and 4 mg strengths. The product was approved in the U.S. in 2015 for the aforementioned indications and is currently in phase III trials for the treatment of agitation associated with Alzheimer's disease and the treatment of PTSD (post-traumatic stress disorder).

(I)

Brexpiprazole is an atypical antipsychotic and shows partial agonist activity at serotonin 5-HT1A and dopamine D2 receptors, and antagonist activity at serotonin 5-HT2A receptors.

WO 2006/112464 A1 discloses piperazine-substituted benzothiophenes, as a class of compounds comprising brexpiprazole, for the treatment of mental disorders such as schizophrenia and other central nervous system disorders. In a general preparation example, a high dose amount of the active benzothiophene compound, thereby forming a major ingredient far exceeding low dose considerations as represented by the approved REXULTI tablets, was mixed with microcrystalline cellulose, corn starch and magnesium stearate and then tableted; the obtained tablet was coated with a film coating. The preparation example is however not suitable for pharmaceutical use.

WO 2012/137971 A1 relates to combinations comprising brexpiprazole and a second drug for use in the treatment of a central nervous system disorder. Among others, tablets for controlled-release release of brexpiprazole for once-daily dosage regimens are exemplified. Accordingly, release of brexpiprazole from the composition is controlled or modified by the presence of a polymer binder, notably cellulose derivative binder. In the specified example, hydroxypropyl methylcellulose (methocel) has been used as matrix polymer.

The marketed product REXULTI is designed as an immediate release tablet, with brexpiprazole being present at low doses as indicated above. For the provision of immediate release, the inactive ingredients of REXULTI tablets include lactose monohydrate, corn starch, microcrystalline cellulose, hydroxypropyl cellulose, low-substituted hydroxypropyl cellulose, magnesium stearate in the tablet core; HPMC (hypromellose), talc and colorants are included in a coating layer. WO 2013054872=EP 2 767 285 A1 provides the technical background for the development of the REXULTI tablets. The tablets are prepared by wet granulation and need disintegrants and a specific polymer binder, hydroxypropyl cellulose, for providing desired disintegration ability. In the examples of EP 2 767 285 A1 an aqueous solution of the polymer binder hydroxypropyl cellulose is added to a powder mixture of brexpiprazole, followed by wet granulation. EP 2 767 285 A1 further discloses that iron oxide included in an outer coating serves for photostability.

While the solubility of brexpiprazole in water is itself limited (0.00227 mg/ml water), the use of hydroxypropyl cellulose and wet granulation for the tablets of REXULTI and as required by EP 2 767 285 A1 may itself compromise the performances in terms of product characteristics, especially delayed disintegration, as well as in terms of technological constraints which in turn affect product characteristics, such as more complex to control preparation conditions and the consequences of using aqueous formulation processings which may encounter stability issues of the active compound brexpiprazole.

It is therefore a hitherto unmet need, and accordingly a problem, to provide a dosage form of brexpiprazole with improved performance and use attributes.

SUMMARY OF THE INVENTION

The present inventors have discovered that unexpected improved performance and use attributes can be attained when an immediate release tablet comprising a limited amount of brexpiprazole in a tablet core is made by direct compression.

The present invention thus provides an immediate release tablet according to claim 1, a batch according to claim 14, and a process for the preparation of an immediate release tablet according to claim 15. Preferred embodiments are set forth in the respective subclaims of the aforementioned claims.

It was surprisingly found that the thus obtained immediate release tablet provides both, short disintegration time combined with short dissolution time, while at the same time allowing simpler formulation technology without the technological constraints associated with EP 2767 285 A1 while allowing elimination of heat and moisture during processing inherent to wet granulation systems, combined with improved content uniformity compared to the granulation technique applied to comparable immediate release brexpiprazole compositions of EP 2767 285 A1. Despite known general challenges involved with direct compression—especially at a relatively low amount of brexpiprazole—compared to the wet granulation technique used in EP 2 767 285 A1, it was found that tablets with excellent immediate release properties and good content uniformity can be obtained in direct compressed tablet cores, even without a need for a granulation binder or even without a need for classical binder substances entirely.

Accordingly, the present invention provides the following aspects, subject-matters and preferred embodiments which, respectively taken alone or in combination, contribute to providing improved technical effects and to solving the afore-mentioned object of the invention:

1. An immediate release tablet comprising at least a tablet core, wherein the tablet core comprises at most 20% brexpiprazole relative to the total weight of the tablet core, and at least one pharmaceutically acceptable excipient, wherein the tablet core is made by direct compression.
2. The immediate release tablet according to item 1, wherein the tablet core is free of binder.
3. The immediate release tablet according to item 1 or 2, wherein the tablet core comprises at most 10% brexpiprazole, preferably at most 5% brexpiprazole, and/or wherein the tablet core comprises tablet strengths of brexpiprazole in a range of from 0.1 mg to 10 mg, particularly in an amount of anyone of 4 mg, 3 mg, 2 mg, 1 mg, 0.5 mg, and 0.25 mg.
4. The immediate release tablet according to any one of the preceding items, wherein the brexpiprazole is having a particle size distribution characterized by a D90 of at most 80 µm, preferably a D90 of at most 75 µm.
5. The immediate release tablet according to anyone of the preceding items, wherein the brexpiprazole is having a particle size distribution characterized by a D50 of at most 25 µm, preferably a D50 of at most 20 µm, and/or having a particle size distribution characterized by a D10 of at most 5 µm, preferably a D10 of at most 2.5 µm.
6. The immediate release tablet according to any one of the preceding items, wherein the tablet core is made by direct compression of a dry powder blend of brexpiprazole and excipient powder.
7. The immediate release tablet according to any one of the preceding items, wherein the water content of the tablet is at most 3.5 wt. %, more preferably at most 3.0 wt. %, measure as loss on drying (LOD).
8. The immediate release tablet according to any one of the preceding items, wherein the bulk density of the dry powder blend prior to direct compression is 0.3 to 0.9 g/ml, preferably 0.4 to 0.8 g/ml.
9. The immediate release tablet according to any one of the preceding items, wherein the Hausner factor of the dry powder blend prior to direct compression is 1.0 to 1.3, preferably 1.05 to 1.2.
10. The immediate release tablet according to any one of the preceding items, wherein the at least one pharmaceutically acceptable excipient in the tablet core is selected from fillers, glidants, disintegrants and lubricants, preferably the tablet core comprises only a filler component, a disintegrant component and/or a lubricant component.
11. The immediate release tablet according to item 10 comprising, relative to the total weight of the tablet core, 0.05 to 20 wt.-%, preferably up to 5 wt.-%, of brexpiprazole, 20 to 90 wt.-%, preferably 50 to 80 wt.-% filler, 0.1 to 20 wt.-%, preferably 2 to 10 wt.-% disintegrant 0.1 to 5 wt.-%, preferably 0.5 to 2 wt.-% lubricant, and 0 to 5 wt.-%, preferably up to 2 wt.-% glidant,
12. The immediate release tablet according to item 10 or 11, wherein the filler component is selected from the group consisting of microcrystalline cellulose or silicified microcrystalline cellulose, lactose such as lactose monohydrate and agglomerated lactose such as Tablettose 70 or Tablettose 80, sugar alcohols and preferably mannitol, erythritol, sorbitol and xylitol, inorganic fillers and preferably anhydrous calcium salt such as calcium hydrogenphosphate, and starches such as maize starch, potato starch, rice starch, wheat starch, pregelatinized starch, fully pregelatinized starch, preferably the filler component is selected from the group consisting of microcrystalline cellulose, silicified microcrystalline cellulose, lactose monohydrate, lactose, and pregelatinized starch more preferably selected from the group consisting of microcrystalline cellulose and agglomerated lactose.
13. The immediate release tablet according to anyone of items 10 to 12, wherein the ratio of D50 of the filler component to D50 of brexpiprazole lies in a range of 10:1 to 0.5:1, more preferably 7:1 to 1:1 and particularly 4:1 to 2:1.
14. The immediate release tablet according to any one of items 910 to 13, wherein the filler component comprises a combination of microcrystalline cellulose with lactose and especially lactose monohydrate, preferably the microcrystalline cellulose has a D50 of 50 µm to 100 µm and the lactose is agglomerated lactose having a particle size distribution wherein 30-70% of the particles are smaller than 200 µm and/or ≥90% are smaller than 63 µm.
15. The immediate release tablet according to anyone of items 10 to 14, wherein the glidant is selected from the group consisting of silicon dioxide, especially colloidal silica, hydrophobic colloidal silica, talc, magnesium silicate and aluminum silicate, preferably fumed silica or Syloid FP silica.
16. The immediate release tablet according to anyone of items 10 to 15, wherein the disintegrant is selected from the group consisting of carmellose calcium, carboxymethylstarch sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, preferably selected from the group consisting of crosslinked polyvinylpyrrolidone (crospovidone), sodium starch glycolate and croscarmellose sodium salt.
17. The immediate release tablet according to anyone of items 10 to 16, wherein the lubricant is selected from the group consisting of stearic acid, talc, sodium stearyl fumarate and magnesium stearate, preferably the lubricant is magnesium stearate.
18. The immediate release tablet according to anyone of the preceding items, wherein prior to direct compression, ingredients to prepare the tablet core are mixed by steps including
    a) mixing the total amount of brexpiprazole with at least one pharmaceutically acceptable excipient to form a first pre-mixture, wherein the brexpiprazole has a particle size distribution characterized by a D90 of at most 80 µm;
    b) adding further at least one pharmaceutically acceptable excipient to the first pre-mixture and mixing, to form a second pre-mixture,
    c) optionally adding further at least one pharmaceutically acceptable excipient to the second pre-mixture and mixing to form a third pre-mixture,
    d) optionally mixing the third pre-mixture with a further pharmaceutically acceptable excipient.
19. The immediate release tablet according to item 18, wherein the weight ratio of brexpiprazole to the at least one pharmaceutically acceptable excipient in step a) is from 1:0.5 to 1:15, preferably the weight ratio is from 1:1 to 1:10, in particular the weight ratio is from 1:1 to 1:5.
20. The immediate release tablet according to item 18 or 19, wherein the at least one pharmaceutically acceptable excipient used to prepare the first, the second and the third pre-mixture at least comprises at least one filler, preferably is a filler or a filler combination, more preferably is a filler component selected from those specified in anyone of items 11 to 13.

21. The immediate release tablet according to anyone of the preceding items, wherein all or essentially all of the brexpiprazole substance in the whole tablet is crystalline.

22. The immediate release tablet according to anyone of the preceding items, wherein all or essentially all of the brexpiprazole substance in the whole tablet is in the form of an anhydrate.

23. The immediate release tablet according to anyone of the preceding items, wherein a D90 of at most 80 µm is controlled by milling original brexpiprazole substance, or by adjustment during crystallization or by size fractionation of originally crystallized brexpiprazole without mechanical impact such as milling.

24. The immediate release tablet according to anyone of the preceding items, wherein the tablet is uncoated.

25. The immediate release tablet according to anyone of items 1 to 22, wherein the tablet core is coated.

26. The immediate release tablet according to item 25, wherein the coating comprises at least one additive selected from the group of film-forming polymers, plasticizers, pigments, glidants, and anti-tacking agents.

27. The immediate release tablet according to item 26, wherein the film-forming polymer additive of the coating is selected from cellulose derivatives, polyvinyl alcohol (PVA) and PVA-based polymers (copolymers of vinyl acetate and vinyl chloride), cellulose derivatives, preferably the cellulose derivative is selected from methyl cellulose, ethyl cellulose, hydroxypropyl cellulose, and hydroxypropyl methyl cellulose, particularly is hydroxypropyl methyl cellulose.

28. The immediate release tablet according to item 26 or 27, wherein the additive of the coating includes a pigment, preferably titanium dioxide, and/or an antitacking agent, preferably talc.

29. The immediate release tablet according to anyone of the preceding items, wherein the tablet core and/or a coating and/or an intermediate layer between the tablet core and an outer coating contains a substance capable of reducing or preventing UV-induced dimerization of brexpiprazole.

30. The immediate release tablet according anyone of the preceding to items, wherein the tablet core and/or a coating and/or an intermediate layer between the tablet core and an outer coating contains a substance selected from:
a substance absorbing UV in a wavelength region of up to 450 nm; in a case when said substance is added to an outer coating, said substance absorbing UV preferably is not iron oxide;
the coating or an intermediate layer forms at least at least 2 wt. %, preferably 2-20 wt. %, more preferably 3-10 wt. % dry coating mass relative to the weight of the tablet core; titanium oxide included in the coating or an intermediate layer around the core is included in an amount of at least 1 wt. % relative to the weight of the tablet core, or when expressed as a weight ratio relative to the weight of brexpiprazole present in the tablet core (TiO$_2$:brexpipratzole) of 0.2:1 or higher, preferably 0.2-3:1, more preferably 0.2-2:1, even more preferably 0.3-1:1.

30. The immediate release tablet according to anyone of the preceding items, which releases at least 75%, preferably at least 80% of the total brexpiprazole content within a period of 45 min, preferably within 30 min.

31. A plurality of immediate release tablets as defined in anyone of items 1 to 30, wherein said plurality comprises at least 10 of said immediate release tablets, wherein the acceptance value of said plurality of immediate release tablets is ≤15.0, preferably ≤10.0, particularly ≤5.0. (the term "acceptance value" is to be determined according to Ph. Eur. 2.9.40).

32. A process for the preparation of an immediate release tablet comprising brexpiprazole, the process comprising:
(i) preparing a tablet core comprising at most 20 wt-% brexpiprazole by direct compression using excipients to provide immediate release;
(ii) optionally applying a coating onto the tablet core of (i).

33. The process according to item 32, which is used to prepare the tablet according to anyone of items 1 to 30, in particular wherein the process comprises, prior to direct compression, mixing of ingredients to prepare the tablet core by steps including
a) mixing the total amount of brexpiprazole having a particle size distribution characterized by a D90 of at most 80 µm with at least one pharmaceutically acceptable excipient to form a first pre-mixture, preferably wherein the weight ratio of brexpiprazole to the at least one pharmaceutically acceptable excipient is from 1:0.5 to 1:15, more preferably the weight ratio is from 1:1 to 1:10, in particular more preferably the weight ratio is from 1:1 to 1:5;
b) adding at least one pharmaceutically acceptable excipient to the first pre-mixture and mixing, to form a second pre-mixture,
c) optionally adding at least one pharmaceutically acceptable excipient to the second pre-mixture and mixing to form a third pre-mixture,
d) optionally mixing the third pre-mixture with a further pharmaceutically acceptable excipient,
e) subjecting the mixture obtained in step c) or d) to direct compression.

34. The process according to item 33, wherein steps c) and/or d) are mandatory steps.

35. A package including one or more tablets as defined in anyone of items 1 to 30 or a plurality of tablets as defined in item 31.

36. The package according to item 35, wherein the packaging material is selected to block, absorb and/or reflect UV exposure up to a wavelength of 450 nm.

37. The package according to item 36, wherein the packaging material comprises aluminum foil and/or polyvinyl chloride (PVC) or polyvinylidene chloride (PVDC) selected to block, absorb and/or reflect UV exposure up to a wavelength of 450 nm.

38. The immediate release tablet as defined in anyone of items 1 to 30 or the plurality of tablets as defined in item 31 for use in the treatment of a central nervous system disease, in particular schizophrenia.

BRIEF DESCRIPTON OF THE DRAWINGS

Further aspects of the invention may be understood from the several drawing views wherein.

Definitions

The term "brexpiprazole" means 7-[4-(4-benzo[b]thiophene-4-yl-piperazine-1-yl)butoxy]-1H-quinoline-2-one respectively the compound of Formula I itself, or a salt thereof. Furthermore, unless specified otherwise by the use of a distinct indication, the term "brexpiprazole" used herein means any physical form including amorphous or crystalline form, and any polymorphic form. The skilled person will appreciate that a reference to "brexpiprazole" further defined by powder characteristics, such as particle size parameters, means a reference to a composition consisting of solid brexpiprazole particles having the defined powder characteristics, such as the indicated particle size distribution.

The skilled person will appreciate that a reference to an excipient, such as a filler, further defined by powder characteristics, such as particle size parameters, means a reference to a composition consisting of solid excipient, such as filler, particles having the defined powder characteristics, such as the indicated particle size distribution.

The specifically indicated term "brexpiprazole anhydrate" as used herein refers to the crystalline form I of brexpiprazole anhydride, disclosed as "anhydride" in WO 2013/162046 A1, which is characterized by having a PXRD comprising reflections at 2-theta angles of 6.8°, 10.0°, 10.8°, 14.5°, 14.9°, 17.4°, 19.2°, 20.3°, 21.3° and 23.2° when measured by copper K$\alpha_{1,2}$ radiation through a monochromator at a wavelength of 0.15418 nm. The crystalline form I of brexpiprazole anhydride can be prepared according to comparative example 1 of WO 2013/162046 A1.

Further, the specifically indicated term "brexpiprazole hydrate" as used herein refers to the crystalline form of brexpiprazole disclosed as "hydrate" in WO 2013/162046 A1 which is characterized by having a PXRD comprising reflections at 2-Theta angles of 7.7°, 9.4°, 11.8°, 18.9° and 24.0°, and preferably further peaks at 2-Theta angles of 5.7°, 8.1°, 8.8°, 10.7°, 12.6°, 13.6°, 13.9°, 15.0°, and 15.6°, when measured by copper Kapha$_{1,2}$ radiation through a monochromator at a wavelength of 0.15418 nm.

The term "brexpiprazole dihydrate" as used herein refers to the crystalline form of brexpiprazole disclosed as "dihydrate" in WO 2013/162046 A1 which is characterized by having a PXRD comprising reflections at 2-Theta angles of 8.1°, 8.9°, 15.1°, 15.6° and 24.4°, and preferably further peaks at 2-Theta angles of 11.6°, 12.2°, 14.0°, 16.3°, 18.1°, 18.4°, 18.9° and 19.5°, when measured by copper Kalpha$_{1,2}$ radiation through a monochromator at a wavelength of 0.15418 nm. Brexpiprazole dihydrate can have a water content according to Karl Fischer of from 6.5 to 8.8 wt. %.

As used herein, batch (or lot) refers to a specific quantity of material produced by a process or a series of processes to a final homogeneous state with specified limits and identified by a batch number and a material number. In the case of continuous production a batch may correspond to a defined fraction of the production. The batch size may be defined either by a fixed quantity or the amount produced in a fixed time interval. The batch can ultimately form or separated into a desired quantity of tablets according to the present invention, typically at least ten.

The term "direct compression" used herein means blending of active pharmaceutical ingredient (i.e. brexpiprazole API), with other ingredients (pharmaceutically acceptable excipients) and direct compaction of the resultant mixture. In direct compression, a dry formulation containing the API brexpiprazole and further ingredients are typically processed by applying a sufficient force by the punches of a tablet press on a powder to compact it into a tablet, notably a tablet core.

The terms "immediate release" (or its abbreviated term "IR") and "immediate release tablet" corresponds to the definition provided in European Pharmacopeia 6.0, part 01/2008: 1502 as relating to "conventional-release dosage forms" or "immediate-release dosage forms" in the form of a tablet showing a release of the active substance (i.e. brexpiprazole API), which is not deliberately modified by a special formulation design and/or manufacturing method, thereby being distinct from "modify-release", "prolong-release", "delayed-release" and "pulsatile-release" dosage forms as defined in European Pharmacopeia 6.0, part 01/2008: 1502. More specifically, "immediate release" or "IR" can mean a release quantity of API of at least 75%, preferably at least 80% within a defined time, such as 60 min or less or typically 45 min or less, as determined according to Ph. Eur. 5.17.1. Measurement conditions are e.g.: paddle, 50 rpm, 0.05 M acetate buffer pH 4.5.

The term "free of binder" used herein means that the brexpiprazole-containing tablet core does not contain a matrix type polymer binder and/or a granulation polymer binder, specifically the tablet core does not contain a cellulose derivative-type polymer binder such as hydroxypropyl cellulose.

The term "essentially" used herein means at least 90%, preferably at least 95% and more preferably at least 98% of the indicated reference (in wt. % if a material is referred to).

For the purpose of this invention, particle size distribution is determined as the percent volume at each particle size and measured by a laser diffraction method in the context of a circulating aqueous suspension. A Malvern Mastersizer 3000 laser diffraction analyzer equipped with a Hydro EV measurement cell is to be used.

For brexpiprazole about 50 mg of sample were filled into a 15 ml glass test tube. The sample was wetted with two drops of Tween 80 and vortexed. Then the thoroughly wetted sample was dispersed in about 7 mL of UHQ-water by vortexing until the particles were dispersed. The suspension was treated for 7 minutes in an ultrasonification bath at RT (Elma S50H). The well dispersed suspension was then measured in water by adding a sample from the center of the test tube containing the well dispersed suspension to a water-filled dispersion unit prefilled with 70 mL of water. The sample in the 70 mL dispersion unit was kept under stirring at 2000 rpm. More sample from the test tube was added, until a targeted obscuration range of 10-25 percent was achieved. The Malvern Mastersizer was operated using the following parameters:

Background time—8 s.
Measurement time—12 s.
Refractive index dispersant—1.33
Stirring unit—2000 U/min (as mentioned above).
External sonification—5 min (as mentioned above)
Internal sonification—no.
Waiting period—3 Minutes.
Diffraction method—Fraunhofer theory.
Analysis model—general purpose.
Sensitivity—normal
Blue laser is on, results are by volume distribution.

Measurement occurred after an optical alignment of the laser was done and after a background measurement was run. A measurement sequence consisted of eight individual measurements for which the mean value was represented as a histogram.

D90 as used herein means that 90% of the particles (based on volume) are smaller than or equal to the indicated size.
D50 as used herein means that 50% of the particles (based on volume) are smaller than or equal to the indicated size.
D10 as used herein means that 10% of the particles (based on volume) are smaller than or equal to the indicated size.

DETAILED DESCRIPTION OF THE INVENTION

The invention is described below in further detail by embodiments, without being limited thereto.

Within the present invention, it has been surprisingly found that an improved immediate release performance with shorter disintegration time can be achieved even without the use of a binder, and accordingly in a preferred embodiment the immediate release tablet preferably does have a tablet core which is free of binder. This contrasts with the need for the tablet core requiring the use of a specific binder, hydroxypropyl cellulose to have a desired disintegration ability, wherein such binder was used to prepare the tablet by wet granulation technology, as described in EP 2 767 285 A1.

Further surprisingly, it was possible according to the present invention to provide an immediate release tablet by direct compression at a controlled low amount of brexpiprazole, notably at most 20% brexpiprazole relative to the total of the tablet core. In accordance with preferred embodiments, it is further possible to provide an immediate release tablet where the tablet core comprises even less amount of brexpiprazole, preferably at most 10% brexpiprazole, more preferably at most 5% brexpiprazole, respectively relative to the total weight of the tablet core. At the same time or alternatively, the amount of brexpiprazole per IR tablet can be defined in absolute terms, such that the tablet core comprises a tablet strength of brexpiprazole in a range of from 0.1 mg to 10 mg, particularly in an amount of 4 mg, 3 mg, 2 mg, 1 mg, 0.5 mg or 0.25 mg brexpiprazole. Contrary to otherwise general expectations of the challenging task to prepare directly compressed tablet cores at such low API contents—all-the-more without using a granulation technique and especially without the use of a polymer binder—, it was possible according to the present invention to obtain an IR tablet where, in the tablet core, brexpiprazole could be homogenously distributed without encountering segregation problems of the powdery blend during tableting.

In a particularly preferred embodiment, which significantly contributes to a control or even complete avoidance of segregation problems, the size of the brexpiprazole substance used as a starting material prior to direct compression is specifically observed. Accordingly, it is preferred that the brexpiprazole substance used for the direct compression step is in the form of particles having a particle size D90 of at most 80 μm, preferably D90 of at most 75 μm. Alternatively or in addition, the defined size of the brexpiprazole substance is characterized by D50 of at most 25 μm, more preferably D50 of at most 20 μm, and/or having a particle size D10 of at most 5 μm, more preferably D10 of at most 2.5 μm.

Moreover, the effective use of making the tablet core by direct compression allows to avoid liquid surroundings and in particular aqueous conditions during the formulation process, which consequently allows to avoid any negative impact of water or moisture or organic liquid impurities as well as to avoid of negative impact of elevated temperature required for drying, and thus translates into favorable properties on product stability. Accordingly, in terms of an overall improved performance in stability and purity, the direct compression involves the use of dry powder blend of brexpiprazole and dry excipient powder. More preferably, the water content of the starting substances for each and every ingredient can be controlled, such as to a level of at most 3.5 wt.-%, more preferably at most 3.0 wt.-%, relative to the total solid mass of the ingredients subjected to direct compression.

A bulk density of the mixture of ingredients used for preparing the tablet core prior to direct compression preferably ranges from 0.3 to 0.9 g/ml, preferably lies in a range of 0.4 to 0.8 g/ml. Moreover, the mixture of ingredients for the tablet core prior to direct compression preferably possesses a Hausner Factor (HF) in the range of 1.0 to 1.3, more preferably 1.05 to 1.2. The Hausner Factor is the ratio of bulk density to tapped density. Achieving and adjusting the afore-mentioned bulk density and Hausner Factor features are advantageous preconditions for the directly compressed brexpiprazole-containing tablet cores.

As the inactive ingredients to be mixed with the controlled amount of brexpiprazole prior to direct compression for preparing the tablet core, at least one pharmaceutically acceptable excipient is suitably selected from the group consisting of fillers, glidants, disintegrants, surfactants and lubricants. Although not being limited thereto, it is preferred that the tablet core contains only the afore-mentioned pharmaceutically acceptable excipients, more preferably the tablet core comprises only a filler component, a disintegrant component and/or a lubricant component, wherein the term "component" means one or more substances from each of the mentioned functional class.

In this context, it is noted that it lies in the nature of pharmaceutical excipients that they sometimes can perform more than one function in a pharmaceutical formulation. In the context of the present invention, in order to provide an unambiguous definitions, the fiction will therefore preferably apply that a substance which is used as a particular excipient, is not simultaneously also used as a further pharmaceutical excipient. For example, a filler such as microcrystalline cellulose used as a filler, is not also used for example as a disintegrant and not also used for example as a binder (even though a microcrystalline cellulose filler might also exhibit a certain disintegrating effect and a certain binding effect) while the term "binder" is meant within the context of the present invention as defined above and which, in particular in the form of a polymer binder and more specifically as a cellulose derivative polymer binder, is preferably avoided as described above.

The filler component may include, without being limited to, a substance selected from the group consisting of microcrystalline cellulose or silicified microcrystalline cellulose, lactose such as lactose monohydrate and (preferably) agglomerated lactose such as Tablettose 70 or Tablettose 80, sugar alcohols and preferably mannitol, erythritol, sorbitol and xylitol, inorganic fillers and preferably anhydrous calcium salt such as calcium hydrogenphosphate, and starches such as maize starch, potato starch, rice starch, wheat starch, pregelatinized starch, fully pregelatinized starch, preferably the filler component is selected from the group consisting of pregelatinized starch, microcrystalline cellulose, silicified microcrystalline cellulose, lactose monohydrate, and lactose, preferably agglomerated lactose such as Tablettose 70.

The glidant may include, without being limited to, a substance selected from the group consisting of silicon dioxide, especially colloidal silica, hydrophobic colloidal silica, talc, magnesium silicate and aluminum silicate, preferably fumed silica or Syloid FP silica.

The disintegrant component may include, without being limited to, a substance selected from the group consisting of carmellose calcium, carboxymethylstarch sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, preferably selected from the group consisting of crosslinked polyvinylpyrrolidone (crospovidone), sodium starch glycolate and croscarmellose sodium salt.

The lubricant component may include, without being limited to, a substance selected from the group consisting of stearic acid, talc, sodium stearyl fumarate and magnesium stearate, preferably the lubricant is magnesium stearate.

It has been found advantageous if an excipient component is adjusted in size in relation to the size of the brexpiprazole component to be combined in the mixture to be subjected to direct compression. This particularly applies with respect to the presence of a filler component, wherein the filler component as mentioned may be a single filler or a combination of fillers. Preferably, the ratio of D50 of one or more fillers (wherein mean size in case of a filler combination means the average mean of all fillers present in the filler component) to D50 of brexpiprazole lies in a range of 10:1 to 0.5:1, more preferably 7:1 to 1:1 and particularly 4:1 to 2:1.

Preferably, the filler component comprises a combination of microcrystalline cellulose with lactose and especially lactose monohydrate, preferably the microcrystalline cellulose has a mean size of about 50 µm (for instance Avicel PH101) to about 100 µm (for instance Avicel PH102) and the lactose is agglomerated lactose having a size of 30-70% being smaller than 200 µm (for instance Tablettose 70) and/or ≥90% of <63 µm (for instance Granulec 230).

In a preferred embodiment, the immediate release tablet according to the present invention comprises, relative to the total weight of the tablet,
0.05 to 20 wt.-%, preferably up to 5 wt.-%, of brexpiprazole, in particular a specific form of brexpiprazole disclosed herein,
20 to 90 wt.-%, preferably 50 to 80 wt.-% filler, in particular a filler disclosed herein,
0.1 to 20 wt.-%, preferably 2 to 10 wt.-% disintegrant, in particular a disintegrant disclosed herein,
0.1 to 5 wt.-%, preferably 0.5 to 2 wt.-% lubricant, in particular a lubricant disclosed herein, and
0 to 5 wt.-%, preferably up to 2 wt.-% glidant, in particular a glidant disclosed herein.

Pharmaceutical compositions comprising a relatively low dose of active pharmaceutical ingredient typically encounters problems of homogeneity of the active ingredient in the composition, especially if made by direct compression. An inhomogeneous distribution of the active ingredient during production of the composition can result both in too high and/or too low content of the active ingredient in the dosage form, which may sequentially lead to an under-dose or over-dose in the patient. Therefore, producing pharmaceutical compositions comprising low dose of active ingredient that have sufficient content uniformity and acceptance value is of high importance. The terms as well as the tests for determining or calculating "content uniformity" and "acceptance value" shall be understood herein as defined in Ph. Eur. 5.2, section 2.9.40 The tests and determinations of content uniformity and the acceptance value relates to the IR tablet when in the form of a tablet core, respectively, i.e. being measured on the tablet core in a status being uncoated. It has been found that the direct compression translates into IR tablet products of the present invention which can have superior acceptance value when compared to products obtained by following a representative prior art description of EP 2 767 285 A, which is surprising since homogeneity would have been more likely and more easily achievable in case of granulated products compared to directly compressed products, especially case of the low dose formulations.

Due to both, the application of direct compression itself and the associated advantageous properties of the mixture of ingredients prior to a bulk compression, which includes relevant factors such as brexpiprazole API size and limited amount of brexpiprazole API—preferably observed in combination with the size of at least a part of the inactive ingredients—, excipient choice (respectively a preferred absence of binder) and the preferred option in the embodiment of step-wise mixing brexpiprazole with excipients, as well as bulk density and Hausner factor of the mixture to thereby establish good flowability and compressibility, the obtained IR tablet possesses excellent disintegration and solubility characteristics as well as homogeneity, and allows good and even remarkably enhanced content uniformity despite low API dose.

Although the preparation of normal physical blends of brexpiprazole with the inactive ingredients (pharmaceutically acceptable excipients) already lead to desirable and advantageous homogeneity of brexpiprazole throughout the tablet core after it had been subjected to direct compression, and thus lead to good acceptance values, it is possible to even further enhance homogeneity and thus further improve content uniformity and acceptance value, if prior to direct compression ingredients to prepare the tablet core are mixed by steps including
 a) mixing the total amount of brexpiprazole having a particle size distribution of d(90) of at most 80 µm with at least one pharmaceutically acceptable excipient to form a first pre-mixture;
 b) adding further at least one pharmaceutically acceptable excipient to the first pre-mixture and mixing, to form a second pre-mixture,
 c) optionally adding further at least one pharmaceutically acceptable excipient to the second pre-mixture and mixing to form a third pre-mixture,
 d) optionally mixing the third pre-mixture with a further pharmaceutically acceptable excipient.

The mixture obtained after step b) and optionally after step c) or d) is then subjected to direct compression. It is preferred that the steps c) and d) are actually carried out. Further preferably, the weight ratio of brexpiprazole to the at least one pharmaceutically acceptable excipient in the first pre-mixing step is adjusted into a particular range, for example by setting a weight ratio from 1:0.5 to 1:15, more preferably the weight ratio is from 1:1 to 1:10, in particular more preferably the weight ratio is from 1:1 to 1:5. In this preferred embodiment of step-wise mixing brexpiprazole with inactive ingredients, the at least one pharmaceutically acceptable excipient used to prepare the first, the second and optionally the third pre-mixture (steps a) to c)) at least comprises at least one filler, preferably is a filler or a filler combination, more preferably is a filler component selected from those specified above. Further excipients can suitably be added in step c) and/or step d), for example disintegrant and/or lubricant can be added in in step c) and/or step d).

Tablets with an improved homogenous distribution and an improved content uniformity of brexpiprazole can be obtained by the step-wise mixing brexpiprazole with inactive ingredients. Being simple and robust and without a need of using a carrier substance or additional process steps to thereby prevent a loss of the active ingredient, a granulating step in the presence of a solvent can be avoided even more effectively. Particularly favourable for low dose brexpiprazole tablets, the suitability of being carried out in low number of mixing vessels will minimize a loss of brexpiprazole when preparing the tablets.

In terms of superior properties of the brexpiprazole substance as such, which is to be included into the IR tablet of the present invention, it is preferred that all or essentially all of the brexpiprazole substance in the whole tablet is crystalline. More preferably, all or essentially all of the brexpiprazole substance in the whole tablet is in the form of an anhydrate. The brexpiprazole anhydrate, which is disclosed as "anhydride" in WO 2013/162046 A1, is for example obtainable according to comparative example 1 of WO 2013/162046 A1. The presence of brexpiprazole anhydrate can be detected by the presence of PXRD peak at 6.0°±0.2° 2-theta and/or the presence of a PRXD peak at 10.0±0.2° 2-theta and/or the presence of a PXRD peak at 17.4±0.2° 2-theta. Another suitable crystalline form is brexpiprazole dihydrate, as disclosed in WO 2013/162046 A1. Still other crystalline forms of brexpiprazole can be used.

As disclosed herein, it is preferred that the brexpiprazole API has a defined particle size. If an originally obtained or prepared brexpiprazole source is larger in particle size than the preferred particle size characteristics of D90, D50 and/or D10 disclosed herein, it is possible to subject such original brexpiprazole source to a size-reduction/comminution treatment, such as milling. However, it was found that milling of brexpiprazole may encounter problems of forming degradation impurities; further, while impurities generated upon milling usually are at a still acceptable level, the level of impurities is further enhanced if fine milled brexpiprazole is exposed to UV light. It was further found that impurity formation, especially photostability issues, may depend on crystal type and particle size of brexpiprazole.

In order to avoid sensitivity towards UV light when fine milled brexpiprazole is used, it is preferred that all or essentially all (such as at least 90 wt. %) of the brexpiprazole substance in the whole tablet is unmilled. To achieve an unmilled state, it is possible to adjust a defined particle size of brexpiprazole by other means, for example by the control of crystal size during the brexpiprazole crystal formation process, i.e. during crystallization or re-crystallization, for instance by adjusting the rate of adding water to the hot brexpiprazole solution, or by adjusting the cooling speed and/or the stirring speed during crystallization when working comparative example 1 of WO 2013/162046 A1. Alternatively or in addition, the lower size of brexpiprazole can be adjusted without mechanical impact such as milling, e.g. by size fractionation such as sieving.

It is possible that the IR tablet according to the present invention consist of the tablet core only, without being coated. Owing to the finding that enhanced UV sensitivity can be controlled, for instance by providing size-defined brexpiprazole without milling, or adding to the IR tablet a substance capable of reducing or preventing dimerization of brexpiprazole as described below, it has become feasible to provide a IR tablet wherein the brexpiprazole has enhanced UV-stability.

Alternatively, the IR tablet of the present invention is coated. This is suitably accomplished by providing one or more coating layers around the tablet core; preferably, a single outer coating layer is provided around the tablet core. Any method for film coating, known in the field of the pharmaceutical technology, may be used; typically the coating is sprayed on the tablet cores as a suspension, the suspension being prepared either by mixing of single excipients or by using ready-made mixtures (e.g. Opadry). The one or more coating(s) comprise at least one additive suitable for preparing the coating layer(s). The at least one additive is preferably selected from the group of film-forming polymers, plasticizers pigments, glidants, andanti-tacking agents. Suitable film-forming polymer additives of the coating(s) may include, without being limited to, a polymer selected from polyvinyl alcohol, hydroxypropyl methylcellulose, hydroxypropyl cellulose, hydroxyethylcellulose and polymethacrylates.

Suitable plasticizers may be selected from the group consisting of triethyl citrate, polyethylene glycol, propylene glycol, dibutyl sebacate, diethyl phthalate, dibutyl phthalate, glycerol monostearate, triacetin, and the like. Further suitable additives the one or more coating(s) include colorants and/or pigments, in particular titanium dioxide, and/or anti-tacking agents, in particular talc. Further, dispersing agents may assist to disperse colorants, pigments and/or minerals to be included into the coating(s).

It was further found that brexpiprazole is affected specifically by a dimerization reaction under UV exposure, specifically encountering a problem of impurity generation by exposure to a wavelength region of 450 nm or below, especially if exposed to UV irradiation/light including UVC from 200 to 280 nm, UVB from 280 to 315 nm and UVA from 315 to 400 nm. As a result of this finding, it has been found that stability against UV-induced dimerization can be strongly enhanced by the incorporation of a substance into the tablet core and/or the one or more coating layers, which substance is capable of effectively reducing or preventing such UV-induced impurity generation and in particular dimerization of brexpiprazole. More effectively, the substance should be capable of reducing or preventing dimerization of brexpiprazole by itself substantially absorbing, reflecting and/or scattering UV light in the aforementioned critical wavelength region to thereby protect brexpiprazole from dimerization. Effective means for reducing or preventing dimerization of brexpiprazole include, but are not limited to dyes and pigments showing UV absorption within the wavelength region of 450 nm or below.

The "means capable of preventing exposure of brexpiprazole to UV light comprising wavelength of up to 450 nm", or the feature "to block, absorb and/or reflect UV exposure in a wavelength region up to 450 nm" means that the brexpiprazole active ingredient is prevented from being substantially exposed to the corresponding critical UV wavelength region. In practice, the said substantially reduced critical UV exposure can be measured by standard transmission tests using a spectrophotometer, for instance as described corresponding pharmacopeiae (e.g. Ph. Eur.) such as in the light transmission test described in USP 37 <671> for containers or likewise adapted for measuring the respectively given substance or material. A suitable substantially reduced critical UV exposure, by virtue of blocking, absorption and/or reflection, is typically achieved if, in such reference spectroscopic light transmission tests the chosen substance or material or substance/material arrangement—when measuring the respective substance or material itself at the ultimately used concentration—exhibits light transmission of at most 70%, and in more preferred options at most 60%, at most 50%, at most 40%, at most 30%, at most 20%, at most 10% and at most 5% in the whole relevant UV wavelength region up to 450 nm.

Preferred and effective means include, without being limited to: Inorganic pigments such as red iron oxide, yellow iron oxide, black iron oxide, zinc oxide and titanium dioxide; organic pigments such as D & C Red 30, D & C Red 34 and D & C Red 36; solvent soluble dyes such as Green 6, D & C Red 17, D & C Violet 2, D & C Yellow 7, D & C Yellow 11, D & C Red 21, D & C Red 27, and D & C Orange 5;

water soluble dyes such as D & C Green 5, FD & C Green 3 (Fast Green), FD & C Yellow 5 (Tartrazine), FD & C Yellow 6 (Sunset Yellow), Quinoline Yellow, D & C Yellow 10, FD & C Red 3 (Erythrosine), D & C Red 22, FD & C Blue 1 (Brilliant Blue), FD & C Blue 2 (Indigotine), FD & C Blue 3, Ponceau 4R, Carmoisine, Naphthol Blue lack, Amaranth, Patent Blue V, Black PN, Orange G, D & C Green 8, D & C Orange 4, FD & C Red 4, D & C Red 28, D & C Red 33, FD & C Red 40, and D & C Yellow 8; and organic lakes such as FD & C Yellow 5 Lake, FD & C Yellow 6 Lake, Erythrosine Lake, D & C Yellow 10 Lake, Quinoline Yellow Lake, D & C Red 21 Lake, Carmoisine Lake, Ponceau 4R Lake, FD & C Blue 1 Lake, FD & C Blue 2 Lake, D & C Red 7 Ca. Lake, FD & C Red 40 Lake, D & C Red 27 Lake, Amaranth Lake, Patent Blue V Lake, and D & C Red 6 Ba Lake. Preferred are the inorganic pigments red iron oxide, yellow iron oxide, black iron oxide and titanium dioxide, and the water soluble dyes FD & C Yellow 5, FD & C Yellow 6, Quinoline Yellow, D & C Yellow 10 and FD & C Red 40. Preferred are pigments and dyes which have their main absorption peak falling in the critical wavelength region up to 450 nm, in particular in the region UVB (280 to 315 nm), UVA (315 to 400 nm) or 400 nm to 450 nm. Also preferred are pigments and dyes which, besides protecting brexpiprazole dimerization, themselves have good light stability, such as iron oxide, titanium dioxide, FD & C Red 40, FD & C Yellow 5 (Tartrazine) and FD & C Yellow 6 (Sunset Yellow). In a case when said substance is added to an outer coating, said substance absorbing UV preferably is not iron oxide.

Effective protection of brexpiprazole from UV-induced dimerization can be particularly accomplished by including said substance in combination with brexpiprazole within the tablet core, or by using of a sufficiently thick coating or intermediate layer which respectively contains said substance such as the mentioned pigments and/or dyes, wherein sufficient thickness can practically be indicated by forming a sufficient coating mass, e.g. at least 2 wt. %, preferably 2-20 wt. %, more preferably 3-10 wt. % dry coating mass relative to the weight of the tablet core.

When specifically and beneficially using titanium oxide as said substance, for an effective protection it is preferably included in the coating or an intermediate layer around the core in an amount of at least 1 wt. % relative to the weight of the tablet core, or as indicated in relation to the amount of brexpiprazole present in the tablet core at a weight ratio ($TiO_2$:brexpipratzole) of 0.2:1 or higher, preferably 0.2-3:1, more preferably 0.2-2:1, even more preferably 0.3-1:1.

When inorganic pigment(s) is(are) used, zinc oxide and particularly titanium dioxide is preferably used as being found particularly effective for blocking brexpiprazole dimerization, and is further preferably chosen in an amount by which reduction and prevention of the brexpiprazole dimerization is significantly enhanced, for instance by adjusting the thickness respectively the dry coating mass and/or the content of titanium oxide as described. Preferred is a coating of at least 2 wt. %, preferably 2-20 wt. %, more preferably 3-10 wt. % dry coating mass relative to the weight of the tablet core, combined with an effective content of titanium oxide present in the coating layer at a weight percentage of more than 10 wt.-%, more preferably more than 20 wt.-%, in particular at least 25 wt.-%, based on the weight of the layer where it is included. Furthermore, according to the concept of reducing or preventing dimerization of brexpiprazole, a pigment or dye as described above may be absent from an outer coating but may be contained in an intermediate layer between the tablet core and the outer layer, or the mentioned pigment or dye can be comprised, or can be included only, within the tablet core but not in a coating around the core. It is for instance effective to correspondingly include pigments such as iron oxide and/or titanium dioxide in such an intermediate layer or in the tablet core.

It has been found that an IR tablet can be obtained according to the present invention which has favorable immediate release characteristics by releasing at least 75%, preferably at least 80% of the total brexpiprazole content within a period of 45 min, preferably within 30 min, as determined according to Ph. Eur. 5.17.1. Suitable measurement conditions for testing are, for instance, using a paddle tester at 50 rpm stirring speed in 0.05 M acetate buffer pH 4.5. Further guidance on dissolution testing is provided in Ph. Eur. 2.9.3 "Dissolution test for solid dosage forms".

More preferably, the IR tablet according to the present invention shows a superior disintegration time, wherein the term "disintegration time" is understood to mean the time until the tablet is disintegrated (disintegration test in accordance with Ph. Eur. 2.9.1). Particularly preferred, the IR tablet according to the present invention shows disintegration time of at most 1 min, more preferably at most 45 sec and particularly at most 30 sec.

Since the IR tablet according to the present invention is made by direct compression, a water content during the formulation process as well as in the finally obtained tablet can be set from the outset and without drying at a lower level compared to tablets produced by wet granulation. An advantageous low water content of the IR tablet according to the present invention is preferably characterized by "loss on drying" (LOD) value of at most 3.5%, preferably at most 3%, more preferably at most 2.5%, determined by testing a pulverized tablet on an IR scale at 100° C. drying after 15 min. That is, when determining 1 g of a pulverized tablet, which at start was accurately weighed, again after 15 min drying at 100° C., the loss in weight is not more than 30 mg, preferably not more than 20 mg, more preferably not more than 10 mg and even less than 5 mg after re-weight the sample after the given drying time.

In a further aspect of the present invention, a plurality of immediate release tablets is provided, wherein the plurality comprises at least 10 of the immediate release tablets disclosed herein, and wherein the acceptance value of said plurality is ≤15.0, preferably ≤10.0, particularly ≤5.0. As described above, the acceptance value can be achieved already by a simple direct compression process, wherein brexpiprazole in the given amount is merely physically blended with pharmaceutically acceptable excipient(s) as inactive ingredients, and the mixture is then subjected to a direct compression step. As further described above, the acceptance value can be further reduced substantially when the total amount of brexpiprazole is mixed, prior to the compression step, by multiple steps with at least a part of the inactive ingredients of the tablet core. This results in an even further improved content uniformity of the IR tablets and the batch thereof according to the present invention.

The present invention further provides a process for the preparation of an immediate release tablet comprising brexpiprazole, the process comprising:
 (i) preparing a tablet core comprising at most 20 wt-% brexpiprazole by direct compression using excipients to provide immediate release;
 (ii) optionally applying a coating onto the tablet core of (i).

As described above already in greater detail, a preferred embodiment of the process resides in that the total amount of brexpiprazole is mixed, prior to the compression step, by multiple steps with at least a part of the inactive ingredients of the tablet core. Accordingly and as described above, the total amount of brexpiprazole is used to prepare a first pre-mixture, and the first pre-mixture is mixed with further at least one pharmaceutically acceptable excipient to prepare a second pre-mixture, optionally followed by further pre-mixing steps, before the thus obtained mixture is subjected to a direct compression step.

The present invention further provides a package including one or more tablets or a batch of tablets as disclosed herein. In order to further improve stability against UV-induced dimerization, the packaging material preferably is selected to block, absorb and/or reflect UV exposure up to a wavelength of 450 nm. This is suitably accomplished by selecting appropriate packing material having the capacity of blocking, absorbing and/or reflecting UV exposure up to a relevant wavelength region of 450 nm. Preferably, the packaging material comprises aluminum foil and/or polyvinyl chloride (PVC) or polyvinylidene chloride (PVDC) selected to block, absorb and/or reflect UV exposure up to a wavelength of 450 nm, or is made of a combined aluminum/polymer foil.

Figure 2:
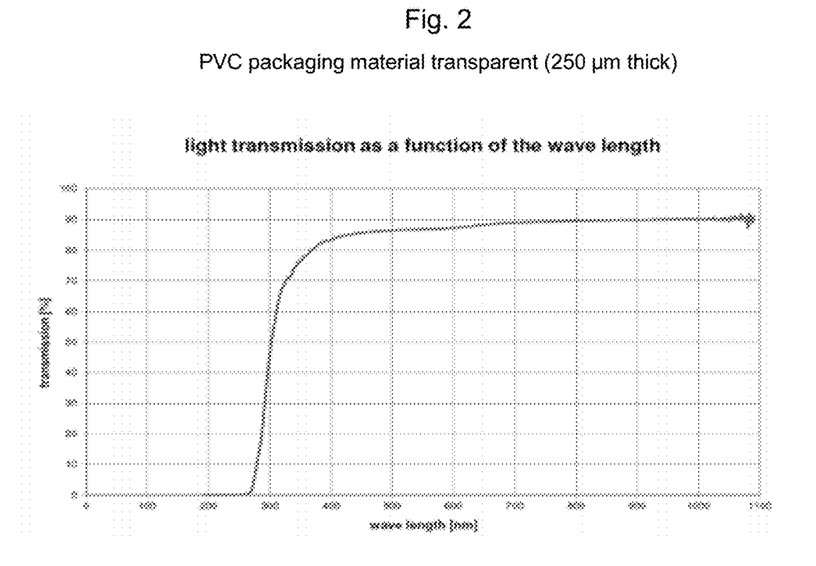
FIGS. 2 and 3 are each graphs illustrating the transmission of various wavelengths of light through PVC packaging materials.
Figure 3:
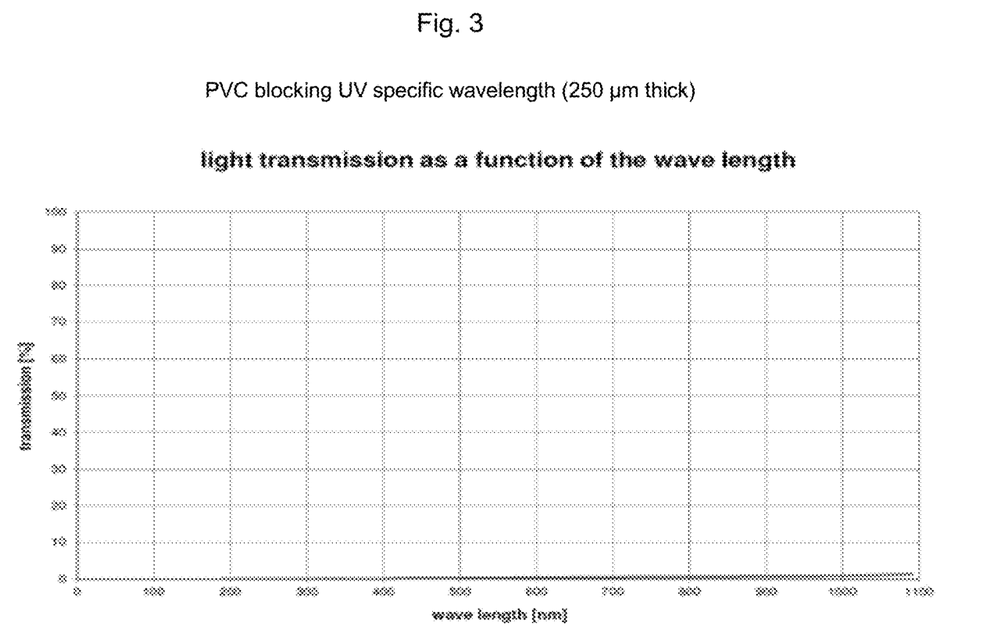

For illustration purposes, reference is made to FIGS. 2 and 3 which show light transmissions depending on the wavelength of two distinct polymer packaging films or foils. While both exemplified polymer packaging films are basically made of PVC (respectively obtained from Klockner Pentaplast, Germany), they differ in their UV specific wavelength absorption and thus UV blocking effect: while normal PVC is transparent in the critical UV wavelength region, in particular UVB (280 to 315 nm) and UVA (315 to 400 nm), as shown in FIG. 2, the specifically selected PVC one for use in the present preferred embodiment does show substantial blocking in the UV-specific wavelength region including UVB and UVA. (FIG. 3). Accordingly, even if the tablets themselves may not be protected from UV-induced impurity formation, the specific UV-induced brexpiprazole dimers can be significantly reduced when packed in the selected packaging materials. And protection from UV-induced dimer formation can be further enhanced if both protection concepts are combined, i.e. the protection by the tablets themselves as described above combined with protection by a selected packaging material.

The immediate release tablet or the batch as described herein is particularly useful in the treatment of a central nervous system disease, particularly for the treatment of schizophrenia, or other CNS disorders.

Other objects, features, advantages and aspects of the present invention will become apparent to those of skill from the present description and examples. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

The present invention is illustrated in the following examples, which should not be construed as limiting.

EXAMPLES

Example 1—Preparation of Brexpiprazole

Crystalline brexpiprazole anhydrate was prepared according to comparative example 1 of WO 2013/162046 A1. Particle size distribution was measured with a Malvern Mastersizer 3000 laser diffraction analyzer as described elsewhere. D90 of the correspondingly measured particle size distribution of the original crystal brexpiprazole powder was determined to be 219 µm.

For further use in subsequent Examples, this original crystal brexpiprazole powder was micronized by a ball mill (7-9 g in 35 ml; 10 min; 25 Hz) to a particle size distribution having a D90 of 66-72 µm.

Example 2—Brexpiprazole API is UV-Sensitive and UV-Sensitivity is Depending on Particle Size Brexpiprazole anhydrate and brexpiprazole dihydrate (the latter having been prepared in accordance with WO 2013/162046 A1) in unmilled state and fine milled as described in Example 1 above were respectively exposed to UV-radiation using an appropriate illumination device (Atlas Suntester XLS+) at 250 W/m$^2$ for 60 hrs, which corresponds to a total UV light intensity of 1350 W·h/m$^2$.

The results are shown in Table 1 below.

TABLE 1

| Sample - Condition | Sum UV-induced Degradation Impurities incl. Brexpiprazole Dimer |
|---|---|
| Anhydrate - unstressed | — |
| Anhydrate - 60 h Suntester | 0.24% |
| Anhydrate - fine milled-60 h Suntester | 1.98% |
| Dihydrate - unstressed | — |
| Dihydrate - 60 h Suntester | 3.06% |

As demonstrated UV-induced dimerization of brexpiprazole depends on particle size. Mechanical stress such as milling enhances the sensitivity towards UV-induced dimerization. The anhydrate form of brexpiprazole is less sensitive to UV-induced impurity generation and dimerization of brexpiprazole than other polymorphic forms.

The UV-induced brexpiprazole dimer impurity can be characterized as follows:

(i) UV-chromatographic RT value of 0.9, using the following HPLC conditions:

| Parameter | Dionex 3000 |
|---|---|
| Column | YMC Pack Pro C18 - 3.0 µm - 100 × 4.6 mm |
| Column Temperature Compartment | 45° C. |
| Solvent A | 0.1% acetic acid pH 2.3/ACN - 85:15 ⇒ Gradient |
| Solvent B | 0.1% acetic acid pH 2.3/ACN - 25:75 ⇒ Gradient |

| *) Gradient | Time [min] | % A | % B |
|---|---|---|---|
| | 0 | 100 | 0 |
| | 25 | 69 | 40 |
| | 30 | 0 | 100 |
| | 30.1 | 100 | 0 |
| | 37 | 100 | 0 |

| Flow | 0.8 ml/min --- p ≈ 107 bar |
|---|---|
| Wavelength | 254 nm |
| Injection Volume | 10 µl |
| Temperature Auto Sampler | RMT |
| Sample Concentration | 0.5 mg/ml |
| Run Time | 37 min --- RT (Brexpiprazole) ≈ 13 min |

(ii) LC-MS molecular weight [M+H]+=867±1, using the following LC-MS measurement conditions:

| MS Tune Parameters | System: HCT ultra |
|---|---|
| Ionization Mode | ESI |
| Polarity | positive |
| Mass Range | 200-2000 |
| MS$^n$-Mode | MS/MS |
| Tune Mass [amu] | 450 |
| Nebulizer Pressure [psi] | 60 |
| Drying Gas Flow [L/min] | 11 |
| Drying Gas Temperature [° C.] | 365 |

(iii) chemical formula $C_{50}H_{54}N_6O_4S_2$,

Example 3—Preparation of Brexpiprazole Containing Tablet by Direct Compression

Tablet cores were prepared by direct compression without polymer binder using the following composition (amounts indicated per tablet):

| | amount [mg] | function |
|---|---|---|
| brexpiprazole anhydr. | 4.0 | API |
| lactose (Tablettose 70) | 44.4 | filler |
| MCC (Avicel PH102) | 36.05* | filler |
| crospovidone | 3.6 | disintegrant |
| Ferric Oxide yellow | 1.35* | pigment |
| Mg stearate | 0.6 | lubricant |
| tablet core | 90.0 | |

Brexpiprazole and the filler components had the following size features:

| | D(90) μm | D(50) μm | D(10) μm |
|---|---|---|---|
| Brexpiprazole | 66-72 | 17-19 | 2 |
| Tablettose 70 | 408 | 205 | 84 |
| Avicel PH102 | 254 | 124 | 41 |

In variations of the compositions (indicated in the ingredient list by *), instead of 1.35 mg differing amounts of 1.5÷2.5 mg Ferric Oxide yellow were incorporated, wherein the increase pigment amount was compensated by a correspondingly decreased amount of MCC filler.

Specifically, brexpiprazole prepared according to Example 1 and being milled to a particle size distribution characteristic of D90 of 66-72 μm was homogeneously mixed with lactose and microcrystalline fillers and with crospovidone, iron oxide and magnesium stearate in the indicated amounts. A batch size of 45 g was produced, corresponding to 500 tablets.

The final blend prior to direct compression showed the following properties:

bulk density: 0.44 tampered density: 0.51

Hausner Faktor: 1.16

Subsequently, the homogeneous mixture was subjected to direct compression.

Compression was carried out with 6 mm round format on excenter press (Korsch XP1) with ~5 kN compression force.

No problems to compress were observed.

Comparative Example 1—Preparation of Brexpiprazole Containing Tablet by Wet Granulation According to EP2767285A/REXULTI Tablet cores were prepared by wet granulation using the following composition (amounts indicated per tablet):

| | amount [mg] | function |
|---|---|---|
| brexpiprazole anhydr.* | 4.0 | API |
| lactose (Tablettose 70) | 44.4 | filler |
| starch 1500 | 20.0 | filler |
| MCC (Avicel PH102) | 10.0 | filler |
| L-HPC (LH-11) | 10.0 | disintegrant |
| HPC (Klucel EF) | 1.0 | polymer binder |
| Mg stearate | 0.6 | lubricant |
| tablet core | 90.0 | |

*compared to Example 3-1 of EP2767285A, dosage strength adapted to 4 mg; composition corresponds to Prescribing Information Rexulti US Specifically, brexpiprazole prepared according to Example 1 and being milled to a particle size of D90 of 66-72 μm was homogeneously mixed with lactose, starch, microcrystalline cellulose and L-HPC in the indicated amounts per tablet (like in Example 2, a batch size of 45 g was produced, corresponding to 500 tablets), including sieving through 0.8 mm and mixing operation for 15 min. A separately prepared aqueous solution of HPC was added to the sieved powder mixture, followed by wet granulation. Granules were sieved via 1.0 mm, dried at 40° C. until LOD≤2% Sieving via 1.0 mm after drying. Mg stearate was added and mixed for further 5 min. Subsequently compression was carried out with 6 mm round format on excenter press (Korsch XP1).

Comparative Example 2—Preparation of Brexpiprazole Containing Tablet by Direct Compression According to WO 2012/137971 (Example 1, Table 3)

Tablet cores were prepared by direct compression using the following composition (amounts indicated per tablet):

| | amount [mg] | function |
|---|---|---|
| Brexpiprazole anhydrate | 30.0 | API |
| Methocel ™ K4M | 52.5 | modified-release agent |
| Avicel ™ PH200 | 66.0 | filler |
| Sodium stearyl fumarate | 1.5 | lubricant |
| tablet core | 150.0 | |

Milled brexpiprazole anhydrate was mixed for 5 min with Methocel K4M, Avicel PH200 and sodium stearyl fumarate (indicated amounts are per tablet) to give a homogeneous blend. A batch size of 75 g was produced, corresponding to 500 tablets. Subsequently the blend was compressed with a 7 mm round punch on an excenter press (Korsch XP1).

Dissolution of the obtained tablets was determined according to Ph. Eur. 2.9.3 using a paddle tester at 50 rpm and a stirring speed in 0.05 M acetate buffer pH 4.5. A sinker device was used to avoid flotation of tablets.

Figure 1A:
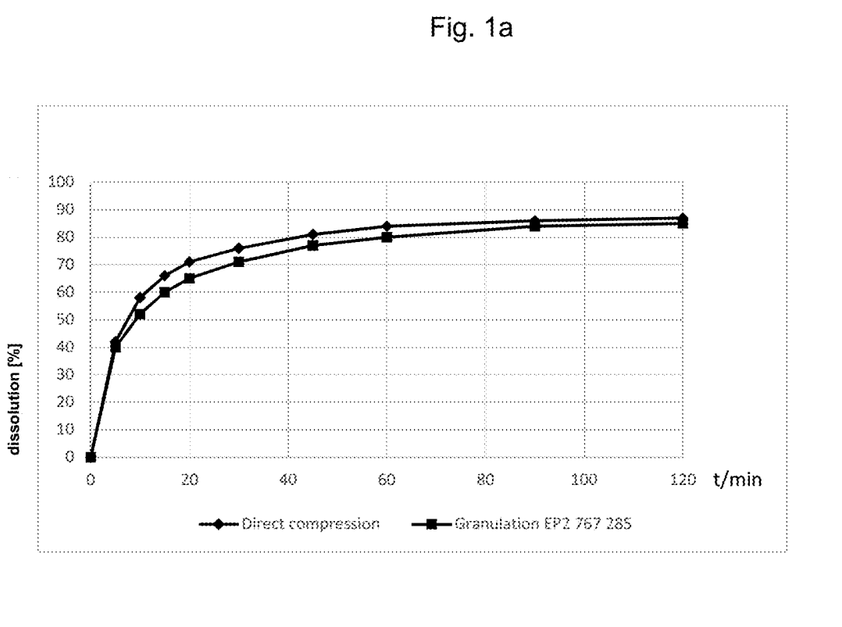
FIGS. 1a and 1b are each graphs comparing the dissolution rate of tablets prepared in accordance with the present disclosure to the dissolution rate of prior art tablets.
Figure 1B:
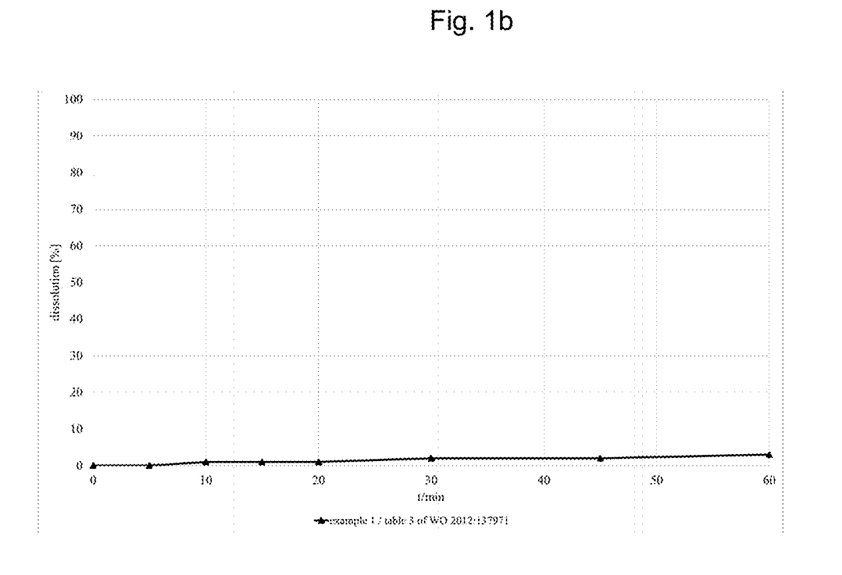

The dissolution results in FIG. 1b show the dissolution profile of a delayed release tablet. Only 3% of brexpiprazole was released after 60 min.

Example 4—Comparison Tests

Results of tests applied to the tablets obtained according to the present invention (Example 2) and in accordance with EP2767285A (representing REXULTI; Comparative Example 1) are shown in the following Table 2:

TABLE 2

|  | wet granulated (comparison corr. to EP 2 767 285 Example 3-1) | direct compressed (invention) |
|---|---|---|
| water content (% loss on drying; LOD)[a] | 4.32 | 2.51 |
| % impurities without irradiation (average of 2 batches) | 1.48 | 1.9 |
| % impurities after irradiation[b] (average of 2 batches) | 4.4 | 3.9 |
| hardness of tablet | 34-54N | 60-70N |
| content uniformity (N = 10 tablets): Acceptance Value (mean; min; max) | 18.7 (85.3; 81.2; 88.4) | 11.2 (109.2; 107.8; 111.7) |
| disintegration test (average of N = 6 tablets) | 45-60 s | 20-30 s |
| dissolution/release of API (paddle, 50 rpm, 0.05M acetate buffer pH 4.5) | see FIG. 1 | |

[a]tablets, originally weighted, were a pulverized on an IR scale at 100° C. drying after 15 min; % LOD indicates the difference in weight after drying
[b]Suntester illumination for 60 hrs (total UV light intensity of 1350 W · h/m$^2$)

It is observed that the tablet according to the present invention made by direct compression showed overall improved performances and use attributes, compared with the wet granulated comparison tablets made in accordance with EP 2 767 285/REXULTI, especially in view of shorter disintegration time, less water content, and improved content uniformity (acceptance value).

Example 5—Preparation of Brexpiprazole Containing Tablet by Direct Compression

| Component | Quantity per unit (mg) | Quantity per batch of 230.000 units (kg) | % |
|---|---|---|---|
| Brexpiprazole | 0.50 | 0.0575 | 0.25 |
| MCC part 1 | 2.50 | 0.460 | 2.00 |
| MCC part 2 | 5.50 | 0.460 | 2.00 |
| MCC part 3 | 61.00 | 7.015 | 30.50 |
| lactose monohydrate | 128.50 | 14.7775 | 64.25 |
| magnesium stearate | 2.00 | 0.230 | 1.00 |
| tablet core | 200.00 | 23 | 100 |

Brexpiprazole obtained and micronized according to Example 1 is mixed with part 1 of microcrystalline cellulose in a 10 liter container for 10 min at 25 rpm to obtain a pre-mixture 1. Microcrystalline cellulose part 2 is added to pre-mixture 1 and further mixed for 10 min at 25 rpm in a 10 liter container to obtain pre-mixture 2. To pre-mixture 2 microcrystalline cellulose part 3 is added and mixed again in a 100 liter container for 30 min at 5 rpm to obtain the pre-mixture 3. Then, lactose monohydrate is added to the mixture and further mixed for 40 min at 5 rpm to obtain a blend. Magnesium stearate is added and the blend is mixed for 10 min at 5 rpm. The blend is compressed to tablets with a target weight of 200 mg. Content uniformity is assessed by drawing 10 samples equally distributed over the whole compression process.

The invention claimed is:

1. An immediate release tablet comprising at least a tablet core, wherein the tablet core comprises at most 20% brexpiprazole relative to the total of the tablet core, and at least one pharmaceutically acceptable excipient, wherein the tablet core is made by direct compression and is free of cellulose derivative polymer binder, and wherein the immediate release tablet has a disintegration time of at most 30 seconds.

2. The immediate release tablet according to claim 1, wherein the tablet core comprises at most 10% brexpiprazole and/or wherein the tablet core comprises tablet strengths of brexpiprazole in a range of from 0.1 mg to 10 mg.

3. The immediate release tablet according to claim 1, wherein the brexpiprazole substance is in the form of particles having one or more of the following size characteristics:
   D90 of at most 80 μm,
   D50 of at most 25 μm, and/or
   D10 of at most 5 μm.

4. The immediate release tablet according to claim 1, wherein prior to direct compression a dry powder blend of brexpiprazole and dry excipient powder meets at least one of the following condition(s):
   the bulk density of the mixture of ingredients is 0.3 to 0.9 g/ml;
   the Hausner Factor of the mixture of ingredients prior to direct compression is 1.05 to 1.65;
   and/or after direct compression the resulting tablet has a value on loss on drying (LOD) of at most 3.5 wt. %.

5. The immediate release tablet according to claim 1, wherein the at least one pharmaceutically acceptable excipient in the tablet core is selected from fillers, glidants, disintegrants and lubricants.

6. The immediate release tablet according to claim 5 comprising, relative to the total weight of the tablet,
   0.05 to 20 wt.-% of brexpiprazole,
   20 to 90 wt.-% filler,
   0.1 to 20 wt.-% disintegrant,
   0.1 to 5 wt.-% lubricant, and
   0 to 5 wt.-% glidant.

7. The immediate release tablet according to claim 5, wherein the at least one pharmaceutically acceptable excipient in the tablet core is defined as follows:
   the filler is selected from the group consisting of microcrystalline cellulose, silicified microcrystalline cellulose, lactose, sugar alcohols, inorganic fillers, and starches;
   the disintegrant is selected from the group consisting of carmellose calcium, carboxymethylstarch sodium, croscarmellose sodium salt, starch, crosslinked polyvinylpyrrolidone, and low-substituted hydroxypropylcellulose;
   the lubricant is selected from the group consisting of stearic acid, talc, sodium stearyl fumarate and magnesium stearate; and/or
   the optional glidant is selected from the group consisting of silicon dioxide.

8. The immediate release tablet according to claim 1, wherein prior to direct compression, ingredients to prepare the tablet core are mixed by steps including
   a) mixing the total amount of brexpiprazole with at least one pharmaceutically acceptable excipient to form a first pre-mixture, wherein the brexpiprazole has a particle size distribution of D90 of at most 80 μm;
   b) adding further at least one pharmaceutically acceptable excipient to the first pre-mixture and mixing, to form a second pre-mixture,
   c) optionally adding further at least one pharmaceutically acceptable excipient to the second pre-mixture and mixing to form a third pre-mixture, d) optionally mixing the third pre-mixture with a further pharmaceutically acceptable excipient.

9. The immediate release tablet according to claim 1, wherein all or essentially all of the brexpiprazole substance in the whole tablet is crystalline.

10. The immediate release tablet according to claim 1, wherein the tablet core is coated, wherein the coating comprises at least one additive selected from the group of film-forming polymers, plasticizers, pigments, glidants, and anti-tacking agents.

11. The immediate release tablet according to claim 1, wherein the tablet further comprises an outer coating and optionally an intermediate layer between the tablet core and an outer coating and wherein the tablet core and/or the outer coating and/or the intermediate layer contains a substance absorbing UV in a wavelength region of up to 450 nm;

wherein the coating or intermediate layer forms at least 2 wt. % dry coating mass relative to the weight of the tablet core; and titanium oxide included in a coating layer or an intermediate layer around the core is included in an amount of at least 1 wt. % relative to the weight of the tablet core, or when expressed as a weight ratio relative to the weight of brexpiprazole present in the tablet core ($TiO_2$:brexpipratzole) at a ratio 0.2-3:1.

12. The immediate release tablet according to claim 1, which has immediate release characteristics by releasing at least 75% of the total brexpiprazole content within a period of 60 min.

13. A batch of immediate release tablets as defined in claim 1, wherein said batch comprises at least 10 of said immediate release tablets, wherein the acceptance value of said batch lies in the range of ≤15.0.

14. A process for the preparation of an immediate release tablet comprising brexpiprazole, the process comprising: (i) preparing a tablet core comprising at most 20 wt-% brexpiprazole and which is free of cellulose derivative polymer binder by direct compression using excipients to provide immediate release; and (ii) optionally applying a coating onto the tablet core of (i), wherein the immediate release tablet has a disintegration time of at most 30 seconds.

15. The process of claim 14, wherein the process further comprises, prior to direct compression, mixing of ingredients to prepare the tablet core by steps including a) mixing the total amount of brexpiprazole having a particle size distribution of D90 of at most 80 μm with at least one pharmaceutically acceptable excipient to form a first pre-mixture;

b) adding at least one pharmaceutically acceptable excipient to the first pre-mixture and mixing, to form a second pre-mixture, c) optionally adding at least one pharmaceutically acceptable excipient to the second pre-mixture and mixing to form a third pre-mixture, d) optionally mixing the third pre-mixture with a further pharmaceutically acceptable excipient, and e) subjecting the mixture obtained in step c) or d) to direct compression.

16. The process of claim 15, wherein the weight ratio of brexpiprazole to the at least one pharmaceutically acceptable excipient in the first pre-mixture is from 1:0.5 to 1:15.

17. An immediate release tablet comprising a tablet core and a coating applied over the tablet core, wherein the tablet core is made by direct compression, is free of cellulose derivative polymer binder, and comprises relative to the total weight of the tablet, 0.05 to 20 wt.-% of brexpiprazole, 20 to 90 wt.-% filler, 0.1 to 20 wt.-% disintegrant, 0.1 to 5 wt.-% lubricant, and 0 to 5 wt.-% glidant, wherein the coating comprises at least one additive selected from the group of film-forming polymers, plasticizers, pigments, glidants, and anti-tacking agents, wherein the tablet releases at least 75% of the total brexpiprazole content within a period of 60 min, and wherein the immediate release tablet has a disintegration time of at most 30 seconds.

\* \* \* \* \*